United States Patent [19]
Spang et al.

[11] Patent Number: 5,560,392
[45] Date of Patent: Oct. 1, 1996

[54] VALVE FOR A MEASURING DEVICE

[76] Inventors: Edmund C. Spang, 47 Elmcrest Rd., Wakefield, Mass. 01880; Hans-Jürgen Postberg, Graf-Stauffenberg-Strasse 5, 63486 Bruchköbel, Germany

[21] Appl. No.: 472,708

[22] Filed: Jun. 6, 1995

[30] Foreign Application Priority Data

Mar. 29, 1995 [DE] Germany ............ 295 50 320.8

[51] Int. Cl.⁶ .................................. F16K 37/00
[52] U.S. Cl. .............. 137/552; 137/554; 137/557; 251/315.11
[58] Field of Search .................. 137/552, 557, 137/551, 554; 251/315.01, 315.11

[56] References Cited

U.S. PATENT DOCUMENTS

| | | | |
|---|---|---|---|
| 2,650,792 | 9/1953 | Marco | 137/552 |
| 4,759,224 | 7/1988 | Charbonneau et al. | 137/552 |
| 5,269,345 | 12/1993 | McHugh | 137/557 |
| 5,406,224 | 4/1995 | McHugh | 137/559 |

FOREIGN PATENT DOCUMENTS

| | | |
|---|---|---|
| 0566210 | 10/1993 | European Pat. Off. . |
| 3809288 | 2/1989 | Germany . |
| 4407689 | 8/1994 | Germany . |
| 2244789 | 12/1991 | United Kingdom . |

*Primary Examiner*—A. Michael Chambers
*Attorney, Agent, or Firm*—Welsh & Katz, Ltd.

[57] ABSTRACT

A valve for a measuring device for the measurement of the physical properties of a fluid in a pipe line has a housing with two coaxial openings for the passage phased in the pipe line. In the housing a valve closure ball is rotatably mounted about a transverse axis. The valve closure ball has a flow channel which, in a first rotary angle position connects to the two openings. In a second rotary angle position turned through about 90° with respect to the first, the valve closure ball blocks the flow between the openings. The piece has a circumferential surface forming a part of a spherical surface, which cooperates with a corresponding valve seating surface on the inside of the valve housing in the manner of a ball valve. In a housing bore coaxial to the axis of rotation of the valve closure ball, which communicates with the flow channel, a sensor is sealingly mounted. In a transverse plane of the valve housing coinciding with the axis of rotation there is a second bore traversing at least the valve housing and the valve seat surface for the connection of at least one second sensor. With this valve it is possible in a simple manner to measure at least two physical properties of the fluid or to carry out a thorough cleaning of the measuring sensor without removing it from the valve.

5 Claims, 1 Drawing Sheet

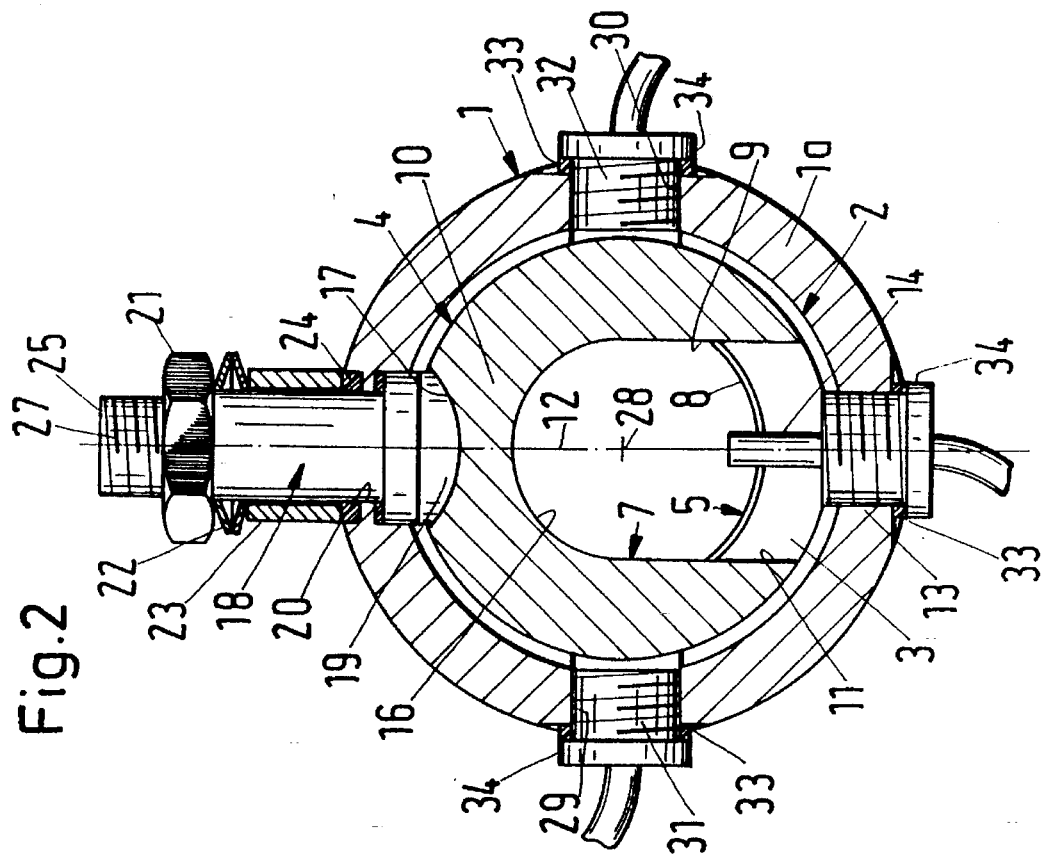
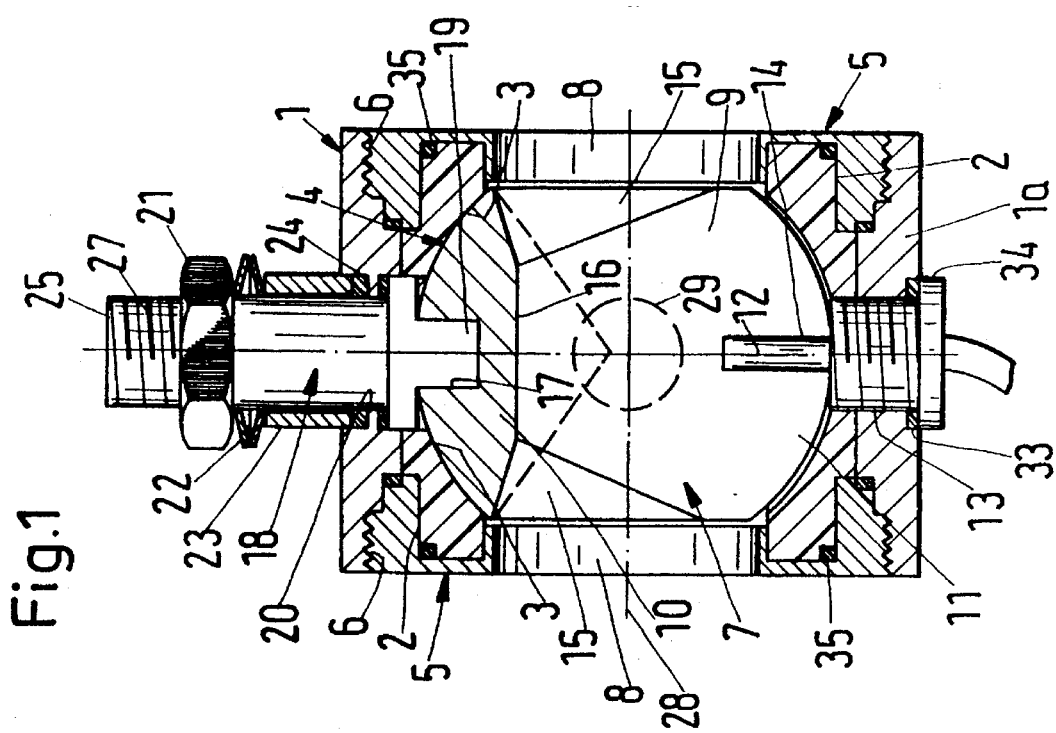

VALVE FOR A MEASURING DEVICE

This invention relates to a valve for use with sensors for the measurement of the physical properties of fluids, such as temperature, pressure, flow rate, pH value, oxygen content, filling state and other properties, in a pipe line or the like.

The valve of the subject invention has a housing which may be installed in a pipe line, which valve has two coaxial openings for the passage of fluid, with a solid valve-closure piece or ball rotatably supported about an axis transverse to the axis of the openings. The ball valve has a flow channel which in a first rotary angle position of the ball valve communicates with both openings, and which in a second rotary angular position turned through about 90° with respect to the first, blocks the flow between the openings. The ball valve has a circumferential surface forming a part of the ball surface which cooperates with a corresponding valve seat surface forming a part of the ball surface on the inside of the valve housing in the manner of a ball valve. A first measuring sensor is located in a bore of the valve housing coaxial to the axis of rotation of the ball, which bore communicates through a break or gap formed by the valve ball with the flow channel; the sensor is sealed in place and the gap is formed continuously in the ends of the flow channel.

A valve of this general type is disclosed in German patent DE 38 09 288 C1. Only one sensor can be connected to this valve. As a result, only one physical property of the fluid flowing through the valve can be measured. If another physical property is to be measured, the sensor must be changed. There are, to be sure, sensors that can measure two different physical properties. Such measuring sensors, however, are expensive and as a rule may be obtained on the market only for pH value measurements with which there is a simultaneous temperature correlation of the pH value. A thorough cleaning of the sensor is then possible only if the sensor is removed from the valve through which the fluid flows.

An object of the subject invention is a valve by which at least two physical properties can be easily measured simultaneously at least two physical magnitudes of the fluid and a more thorough cleaning is possible without removal of the sensor from the valve.

SUMMARY OF THE INVENTION

According to the subject invention there is a valve that has a transverse plane of the valve housing which coincides with the axis of rotation of the valve, a second bore traversing the valve housing and the valve seat surface for the connection of a second measuring sensor.

With this structure at least two physical properties of a fluid can be measured simultaneously by the two measuring sensors. In the closed state of the valve then, both measuring sensors can be removed, so that the interior space of the valve can be cleaned by a pressurized fluid which is pumped from a pressure source connected to the bore into the interior space of the valve and out again through the other bore. It is then possible to check the accuracy of the one sensor, for example after a relatively long period of operation, by removing the other sensor and, through a connecting bore, pumping a fluid with a known value for the physical property being measured into the interior of the valve. If the actual measured value does not agree with the known value, the sensor must be recalibrated or changed.

In a further development care is taken that in the transverse plane mentioned a third bore traversing the valve seating surface is used for the connection of a third measuring sensor. With this embodiment three measuring magnitudes can be measured simultaneously.

It is then possible to use the first bore for the connection of a pressure, flow, pH or other sensor and the second bore for the connection of a temperature sensor. In this manner it is possible to carry out temperature compensation of the measured value in a measurement converter engaged on the outlet side of the two sensors, for example, with an electronic computer, which compensation is detected by the sensor connected to the first bore and is dependent on temperature.

In this embodiment, a third bore can be formed in the valve body for the attachment of a pressure sensor. In this manner it is possible, when the sensor connected to the first bore measures the flow, pH value or the concentration of a certain gas in the fluid, to correct the measurement values of the first and third sensors simultaneously in correlation to the temperature measured by the second sensor.

An advantageous further development is the valve seat surface which is formed by at least one slip ring arranged between the openings of the valve housing, and that between the security rings and the slip ring (or slip rings) there is an elastic sealing ring. The sealing rings bring about not only a positive seal between the security rings and the slip ring or slip rings, but also a sealing between the slip ring or slip rings and the ball in the area of the valve seat surface.

BRIEF DESCRIPTION OF THE DRAWINGS

The invention and its further developments are described in detail below with the aid of the drawing of a preferred embodiment.

FIG. 1 is an axial section through a valve according to the subject invention and FIG. 2 is a cross section through the valve according to FIG. 1 along the axis of rotation of the valve ball.

DETAILED DESCRIPTION OF THE PREFERRED EMBODIMENT

The valve represented has a valve housing 1 with an outer substantially cylindrical housing part 1a, slip rings 2 of synthetic material such as polytetrafluoroethylene (PTFE) installed therein, the spherical segment shaped inner surfaces 3 of which form the valve seat for a partly spherical valve closure piece or vane 4. For the axial fastening of the slip rings 2 there are fastening rings 5 which have an outside thread and are screwed into coaxial threaded bores 6 of the housing part 1a. The slip rings 2 are axially separated, but can also be constructed in one part. Instead of being made of plastic they can also be metal.

The valve vane 4 has a flow channel 7 which follows upon the openings 8 of the security rings 5. The openings 8 simultaneously form openings of the valve housing 1. The flow channel 7 is bounded by side walls 5, a web 10 connecting the side walls 9, and the slip rings 2. On the side away from the connecting web 10 of the valve ball 4 the flow channel 7 is provided with a passage 11 which is continuous in its direction of flow. The valve ball 4 is borne rotatably in the housing 1 about a rotary axis 12 running perpendicular to the flow direction and through the middle of the passage 11.

Coaxially to the axis 12 of rotation there is formed in the housing 1 a bore 13 with an inside thread. The bore 13 receives a sensor 14 for the measuring of a physical property, such as of the flow, pH value or oxygen content of the fluid flowing through the flow channel 7.

The web 10 projects radially inward in the axial section as shown in FIG. 1, in which arrangement the cross section of the end sections 15 of the flow channel 7 on the side lying opposite the passage 11 narrows conically from the ends of the flow channel and forms between these end sections 15 a part 16 of a circular cylinder.

In order to turn the valve ball 4, in a transverse slit 17 of the web 10 there is an actuating shaft 18 with a flat end section 19. The actuating shaft 18 passes through a further bore 20 of the housing 1 coaxially to the axis of rotation 12, in which it is rotatably borne, sealed against the bore 20. A security nut 21 screwed onto a threaded section of the shaft 18 is supported over plate springs 22, a sleeve 23 and a seal 24 on an inner shoulder of the bore 20. The outer end 25 of the shaft 18 is provided with a thread 27 for the placement of an actuating lever (not shown).

The valve of the subject invention can be installed in a pipe line (not shown), so that the openings 8 follow closely upon the free end of the pipe line. In the open position represented of the valve the fluid flowing through the pipe line, which is generally a liquid, can flow further through the flow channel 7, where it is deflected by the first-traversed conical end section 15 and the radially inward projecting web 10 in the direction to the bore 13 or the measuring sensor 14, without the projection of the web 10 disrupting the flow of the fluid. The length of the sensor 14 regardless of the inside diameter of the pipe line or of the openings 8, needs only to be such that it comes in contact with the fluid in the flow channel 7, since the wall thickness of the housing 1 is independent of the inside diameter or the wall thickness of the pipe line. Possible dirt particles in the fluid which tend to settle near the bore 13 in the lower hollow space region of the flow channel 7 are carried along by the flow of the fluid when the valve is open. Even with the installation position of the housing 1 turned through 180° about the longitudinal axis 2B of the housing 1 with respect to the position represented, the danger is small that in the case when the fluid is a liquid, in the vicinity of the bore 13 an air bubble will form, because this, too, would be carried along by the fluid flow.

In one embodiment the web 10 could be formed projecting still further inward, as it is represented by the broken lines in FIG. 1. Thus a strong deflection of the flow would still be present in the direction toward the measuring sensor 14. However, this construction would disrupt the flow somewhat more than in the if the circular cylinder part 16 were used.

In a transverse plane of the valve housing 1 coinciding with the axis of rotation 12 standing perpendicular to the flow direction or the axis 28, there are formed two further bores 29 and 30 with an inside thread. These bores 29, 30 pass through the valve seat surface 3 and are constructed for the connection in each case of a further sensor 31 and 32 with an outside thread. Sensors 31 and 32 do not have to come directly in contact with the fluid flowing through the flow channel 7. If the sensor 14 is, for example, a pressure, flow, pH-value or gas, e.g. oxygen, sensor where, for example an oxygen sensor, with which the measurement value depends on the temperature of the fluid, it is possible, for example, for the sensor 31 to be a temperature sensor. If need be, a converter can be engaged on output side of the sensors 14 and 31; for example the converter could be a computer which corrects the measured value of the sensor 14 dependent on the temperature measured by the sensor 31 before display of the measured valve. Even if the two slip rings 2 are not separated but constructed in one part, the temperature sensor 31 nevertheless, also in the open position of the valve closure piece 4, as it is represented in FIGS. 1 and 2, would indirectly measure the temperature of the fluid.

Alternatively, sensor 31 can be constructed as a pressure sensor. In this case, too, the sensor 31 can measure the pressure with valve open, as shown in the drawings, since the pressure of the fluid, even with one-part construction of the slip rings 2, would be propagated through the gap between the valve ball 4 and the slip ring 2 or the slip rings 2 up to the pressure sensor.

The sensor 32 can likewise be a temperature sensor or pressure sensor. Expediently the sensor 31 is a temperature sensor, the sensor 32 is a pressure sensor and the sensors 14 is a flow, pH-value or gas sensor, so that three physical properties of the fluid can be simultaneously measured and the readings of the sensors 14 and 32 can be instantaneously temperature-compensated.

It is also possible, however, to provide three pressure sensors, for example for safety reasons in nuclear power plants, with which the measurement values of the three measuring sensors are compared by a comparator for checking as to deviations; a deviation would then be established and reported in order to find errors or faults in the measuring arrangement.

The bores 29 and 30 have the further advantage that with a closed valve, i.e. when the valve ball 4 has been turned through 90° with respect to the position represented, and after removal of the sensors 31 and 32, the valve may be rinsed through the bores 29 and 30 in order to clean the sensors 14 of possible deposits without the necessity of removal from the valve.

Similarly, with the valve closed one of the sensors can be unscrewed, in which process the pressure prevailing on the closure ball 4 can be gradually lowered, and in its place a pressure source with known pressure can be connected in order to check the accuracy of one of the two other sensors which may be a pressure sensor. In the same manner the accuracy of the other measuring sensors can also be checked by connecting a fluid source with known physical properties of the fluid to a bore.

Possible leaks between the bores 13, 29 and 30 and the sensors 14, 31, 32 are sealed by sealing rings 33 between a flange 34 or a shoulder of each measuring sensor and flat surfaces which surround in each case one of the opening edges of the bores 13, 29 and 30.

Between the slip rings 2 and annular grooves formed in the insides of the security rings 5, in which the slip rings 2 engage, elastic sealing rings, such as O-ring 35 are used. These sealing rings 35 allow, mainly with the valve closed, the slip rings 2 to seal not only the security rings 5, but also the valve ball 4, mainly on the side of the valve ball 4 facing the fluid pressure. Thus the valve ball 4 in the closed position is pressed tightly under the fluid pressure against the one slip ring, and away from the other slip ring 2. The sealing ring 15 arranged between the other slip ring 2 and the associated security ring 5 then presses the slip ring 2 lying on the fluid pressure side against the valve ball 4 and this results in a better sealing action.

It would be possible to use the separated slip rings 2, a one-part slip ring. However, with such a construction, the installation of the valve ball 4 in the slip ring may be difficult; with sufficient elasticity of the slip ring and greater diameter of the valve ball 4, such could be done; with the use of the sealing rings 35 there would be the same advantages as with separated slip rings.

A further modification of the subject invention can lie in that the actuating shaft 18 has a soft blind bore, in which a further temperature sensor can be introduced.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

What is claimed:

1. A valve for a device for measuring the physical properties of a fluid in a pipe line said valve having a valve housing in the pipe line, said housing having a first and second coaxial openings for the passage of the fluid a valve closure means rotatably mounted about an axis extending transversely to the axis of said openings a flow channel in a first rotary angle position of said valve closure comprising an open passageway between each of said first and second openings, and in a second rotary angle position turned through about 90° with respect to the first rotary angle position, comprising a closed passageway between the openings said valve closure means having a circumferential surface forming a part of a spherical surface which cooperates with a corresponding valve seat surface forming a spherical surface on the inside of the valve housing in the manner of a ball valve a first sensor means sealingly mounted in a first bore of said valve housing coaxial to the axis of rotation of said valve closure means said first bore communicating through a passageway of said valve closure means with said flow channel, said passageway of said valve closure means being continuous between the ends of said flow channel whereby in a transverse plane of said valve housing coinciding with the axis of rotation, there is a second bore traversing said valve housing and the valve seat surface for the connection of a second sensor means.

2. The valve of claim 1, further including a third bore traversing said valve housing and said valve seat surface for the connection of a third sensor means.

3. The valve of claim 1, whereby said first bore is for the connection of a pressure, flow, pH or gas sensor, and the second bore is for the connection of a temperature sensor.

4. The valve of claim 2, whereby said third bore is for the connection of a pressure sensor.

5. The valve of any of claim 1 whereby, said valve seat surface is formed by security rings, and at least one slip ring between said security rings bounding said coaxial openings of said valve housing, and between said security rings and said slip ring is an elastic sealing ring.

* * * * *